United States Patent [19]

Cerny et al.

[11] 4,321,380
[45] Mar. 23, 1982

[54] ALKYL CYANOMETHYL ERGOLINE-I DERIVATIVES AND SALTS THEREOF, AND METHODS FOR THEIR PREPARATION

[75] Inventors: Antonin Cerny; Miroslav Semonsky; Rudolf Kotva; Karel Rezabek; Marie Auskova; Miroslav Seda, all of Prague, Czechoslovakia

[73] Assignee: SPOFA, United Pharmaceutical Works, Prague, Czechoslovakia

[21] Appl. No.: 749,995

[22] Filed: Dec. 13, 1976

[30] Foreign Application Priority Data

Dec. 12, 1975 [CS] Czechoslovakia ............ 8472-75

[51] Int. Cl.$^3$ ............................................ C07D 457/02
[52] U.S. Cl. ............................................ 546/67; 424/261
[58] Field of Search .................... 260/285.5; 546/67

[56] References Cited

U.S. PATENT DOCUMENTS

| | | | |
|---|---|---|---|
| 3,732,231 | 5/1973 | Semonsky et al. | 260/285.5 |
| 3,880,856 | 4/1975 | Bach et al. | 260/285.5 |
| 3,920,664 | 11/1975 | Clemens et al. | 260/285.5 |
| 3,959,288 | 5/1976 | Bach et al. | 260/285.5 |
| 3,992,385 | 11/1976 | Bach et al. | 260/285.5 |
| 4,005,090 | 1/1977 | Semonsky et al. | 260/285.5 |

FOREIGN PATENT DOCUMENTS

1199233 7/1970 United Kingdom ............ 260/285.5

OTHER PUBLICATIONS

Krepelka et al., *Collection of Czechoslovak Chemical Communications*, vol. 42, (1977), pp. 2953–2956.

*Primary Examiner*—Mary C. Lee

[57] ABSTRACT

A procedure is described for the preparation of a novel group of alkyl cyanomethyl ergoline-I derivatives and pharmaceutically acceptable salts thereof. The compounds are D-6-alkyl-8-cyanomethylergoline-I derivatives of the formula

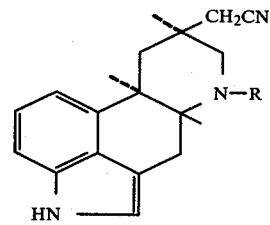

wherein R is an alkyl group of 2–4 carbon atoms.

7 Claims, No Drawings

ALKYL CYANOMETHYL ERGOLINE-I DERIVATIVES AND SALTS THEREOF, AND METHODS FOR THEIR PREPARATION

This invention relates to ergoline derivatives. More particularly, the present invention relates to alkylcyanomethyl ergoline-I derivatives and to a process for the preparation thereof.

During the past decade, there has been a birth of interest within the pharmaceutical industry in a class of compounds which evidence prolactin inhibition and antinidation characteristics, so suggesting their use in human and veterinary therapy.

In accordance with the present invention, a procedure is described for the preparation of a novel group of alkylcyanomethyl ergoline-I derivatives and pharmaceutically acceptable salts thereof which have been found to inhibit prolactin secretion of gonadotropins, the former characteristic being manifested as an antinidation and antilactation effect and the latter by the ability to induce oestrus. The novel compounds described herein may be classified as D-6-alkyl-8-cyanomethylergoline-I compounds of the formula

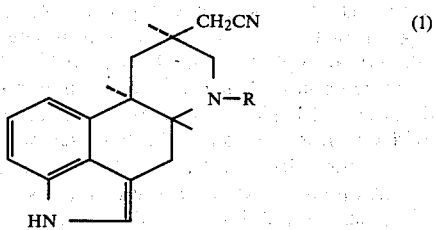

wherein R is an alkyl group, either straight or branched chain, of 2-4 carbon atoms. Studies of the described compounds have revealed that the activity thereof with respect to both prolactin inhibition and gonadotropin secretion is significantly higher in certain cases than the activity of prior art compositions such as those described in U.S. Pat. No. 3,732,231 and Belgian Pat. No. 811,610.

The cyanomethylergoline-I derivatives herein may conveniently be prepared by (I) reaction of D-8-cyanomethylergoline-I of the formula

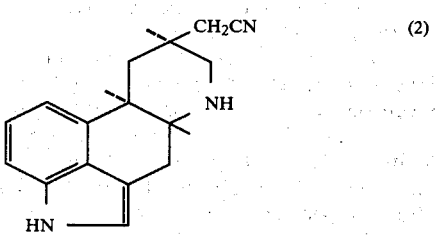

with an alkylation agent of the formula X—R wherein R is an alkyl group, either straight or branched chain, of from 2-4 carbon atoms and X is selected from the group consisting of (a) a halogen atom,
(b) a moiety of a sulfonic acid, either aromatic or aliphatic, and
(c) a sulfuric acid moiety, or (II) reaction of an ester of D-6-alkyl-8-hydroxymethylergoline-I of the formula

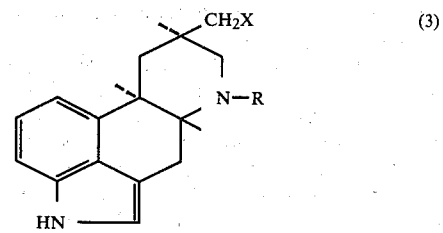

wherein X and R are as designated above with an alkali metal cyanide. The resultant composition of formua (1), above, may then be converted to a pharmaceutically acceptable addition salt by reaction with an acid.

Turning first to the aforementioned alkylation reaction, this end may readily be attained by reacting the alkylation agent with the 6-nor derivative of formula (2), above, in an inert organic solvent, in the presence or absence of an acidbonding agent at temperatures ranging from 0°-150° C. A general preference has been found for a temperature range of 20°-100° C. Solvents found to be of particular interest for this purpose include ethanol, ethylene glycol, ethylene glycol dimethyl ether, dimethylformamide, dimethylsulfoxide, hexamethylphosphoric triamide and the like.

Alkylation agents employed herein may be chosen from among the alkyl chlorides, bromides and iodides, esters of sulfonic acid such as methanesulfonates, p-toluenesulfonate and the like, or esters of sulfuric acid such as diethyl sulfate.

The acid-bonding agent whose use herein is optional may be either organic or inorganic bases. Typical of the former are tertiary amines such as triethylamine, N-methylpiperadine and the like. Suitable inorganic bases include the carbonates of sodium, potassium and calcium. Acid formed during the course of the reaction can be neutralized with the D-8-cyanomethylergoline-I employed as a starting material.

The duration of the alkylation reaction is dependent upon several factors, namely, the reactivity of the alkylating agent chosen and the temperature of reaction. Thus, the duration may range from several hours to several days.

It should also be noted that D-8-cyanomethylergoline-I, formula (2) above, is a novel compound which may be prepared by reacting D-6-methyl-8-cyanomethylergoline-I with cyanogen bromide at room temperature in an inert solvent such as dichloromethane or chloroform to yield D-6-cyano-8-cyanomethylergoline-I of the formula

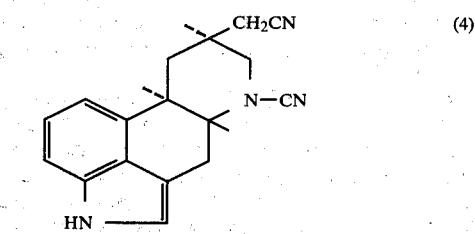

by reduction or hydrolysis, selective reduction of the 6 organo group being the preferred procedure. Reduction may readily be effected with hydrogen in the presence of a catalyst such as Raney nickel in the presence of an organic solvent such as dimethylformamide, or by the action of zinc in acetic acid. Alternatively, this end may be attained by reaction with sodium borohydride in methanol or pyridine.

Returning now to the alternative technique for preparing ergolines herein (reaction II), a reactive ester of D-6-alkyl-8-hydroxymethylergoline-I of formula (3) is reacted with an alkali metal cyanide such as cyanide of sodium or potassium in an inert solvent of the type described above (in reaction I) at a temperature ranging from 20°–160° C., a general preference being found for temperatures ranging from 100°–130° C.

The esters of formula (3) may be selected from among the corresponding halides or the sulfonic acid esters. The chloride and an ester of p-toluenesulfonic acid are of particular interest for this purpose. Once again, it is to be noted that these compounds, that is, the esters of formula (3) are novel compounds. They may readily be obtained by alkylation of the methyl ester of D-6-nor-9,10-dihydrolysergic acid (prepared according to T. Fehr et al, Helv. Chim. Acta 53, 2197 (1970)) with an alkyl halide to yield a D-6-nor-6-alkyl-9,10-dihydrolysergic acid methyl ester of the formula

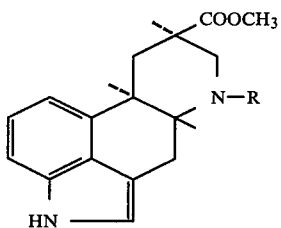

wherein R is as stated above, the methyl ester being reduced to yield the corresponding D-6-alkyl-8-hydroxymethylergoline-I of the formula

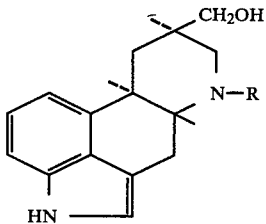

wherein R is as stated above. The hydroxy compound (6) is then converted to the reactive ester of formula (3).

Alkylation of the aforementioned methyl ester may be implemented with a corresponding alkyl halide, typically the bromide or iodide, in an inert organic solvent such as dimethylformamide in the presence of an acid bonding agent such as potassium carbonate. This reaction is carried out at a temperature ranging from 20°–100° C.

Reduction of compound (5) to compound (6) is effected by means of complex metal hydrides in an inert organic solvent. Hydrides suitable for this purpose include lithium aluminum hydride, sodium bis-(2-methoxyethoxy) aluminum hydride, sodium borohydride and the like. A preferred material is lithium aluminum hydride in anhydrous diethyl ether or tetrahydrofuran.

The 8-hydroxymethyl derivative of formula (6) may be converted to the reactive ester of formula (3) by chlorination of the former with reagents such as phosphorous pentachloride, phosphorous oxychloride, thioxyl chloride and the like at elevated temperatures. A preferred procedure for effecting this end involves reacting a D-6-alkyl-8-hydroxymethylergoline-I of formula (6) with an excess of phosphorous oxychloride at the boiling point of the reaction mixture.

Pharmaceutically acceptable addition salts of D-6-alkyl-8-cyanomethylergoline-I compounds of formula (1) may be prepared by reacting at least 1 mole-equivalent of an inorganic or organic acid with 1 mole-equivalent of ergoline-I in a solvent. Solvents found suitable for this purpose are methanol, ethanol, water and mixtures thereof. Acids employed in this reaction may be chosen from among sulfuric, hydrochloric, hydrobromic, methanesulfonic, tartaric, maleic, citric and the like acids.

As noted previously, the novel ergoline-I derivatives described herein evidence pharmacological activity which suggests their use in human and veterinary therapy. From the pathophysiological point, the novel compounds can be advantageously employed therapeutically in any case wherein it is desirable to decrease the prolactin level or to increase the level of gonadoptropins in the blood system of animals or humans. Typical of such applications are termination of postpartum lactation, galactorrhea, acromegalia, cerebral lesions of organic origin, hypertrophy or carcinoma of the prostate, certain hypofunctional states of the gonads, etc.

Based upon studies made with compounds of the type described, it has been concluded that such compounds evidence an exceptionally high antilactation activity in rats. Thus, for example, D-6-n-propyl-8-cyanomethylergoline-I evidences significant activity at a dosage of 10 μg/kg and D-6-ethyl-8cyanomethylergoline-I is still active at a dosage of 100 μg/kg.

Antilactation effect is lactating female Wistar rats was assessed from the weight gain and survival of the sucklings, as well as from the degree of filling of their stomachs with milk on the basis of evaluation of the "milk spots" (see method described by L. Flueckiger, H. R. Wagner: Experientia 24, 1130 (1968); M. Auskova, K. Rezabek, M. Semonsky: Arzneimittelforsch., 4, 617 (1973).

In the case of D-6-isobutyl-8-cyanomethylergoline-I a significant stimulating effect was found on the secretion of gonadotropins. Stimulation of secretion of pituitary gonadotropins was assessed from the degree of hypertrophy of the ovary remaining after a unilateral ovariectomy of adult female rats (see Benson et al, Endocrinology 84, 369 (1969).

Several examples of the application of the present invention are set forth below. It will be appreciated by those skilled in the art that the examples are for purposes of exposition only and are not to be construed as limiting. The melting points of the compound were determined on a Kofler block and are given in 0° C., all other temperatures being in the same temperature system. Given values of specific rotation relate to compounds which are free of crystal solvent.

EXAMPLE 1—D-6-n-propyl-8-cyanomethylergoline-I 210 mg (1.5 mmoles) of anhydrous potassium carbonate and 184 mg (1.5 mmoles) of n-propyl bromide were added to 251 mg (1 mmole) of D-8-cyanomethylergoline-I in 10 ml of anhydrous dimethylformamide and the mixture stirred at 65° C. for 24 hours. The major portion of the dimethylformamide solvent was distilled off under reduced pressure and the residue mixed with 25 ml of water. Then, the mixture was made alkaline by the addition of ammonia, the pH thereof ranging between 7.5 and 8. The resultant crude product was filtered (280 mg; 96%) and chromatographed on a silica gel column using a 9:1 chloroform-ethanol mixture as eluant. Crystallization from ethanol yielded pure D-6-n-propyl8-cyanomethylergoline-I as colorless needles, m.p. 264°-266° C. (decomposition) $[\alpha]_D^{20} - 83°$ C. (C=0.4 pyridine).

Hydrogen tartrate of the foregoing base was prepared by dissolving 293 mg (1 mmole) of D-6-n-propyl-8-cyanomethylergoline-I in 20 ml of a hot aqueous solution of tartaric acid (300 mg, 2 mmoles). The water was distilled off under reduced pressure and the salt crystallized from ethanol, m.p. 207°-210° C. (decomposition).

The D-8-cyanomethylergoline-I employed was prepared by adding 0.7 grams (6.5 mmoles) of cyanogen bromide to a solution of 1.33 grams (5 mmoles) of D-6-methyl-8-cyanomethylergoline-I in 175 ml of methylene chloride and stirring the mixture at room temperature for 2 days. A small portion of the separated compound was filtered, the filtrate extracted with a 10% tartaric acid solution and the organic layer removed under reduced pressure. The residue was crystallized from 95% aqueous alcohol and yielded 0.8 gram of D-6-cyano-8-cyanomethylergoline-I as colorless needles, m.p. 276°-278° C. (decomposition); $[\alpha]_D^{20} + 46°$ C. (C=0.4 pyridine). 3.4 grams of zinc powder was added to a solution comprising 0.60 gram of the above-described D-6-cyano derivative in a mixture comprising 120 ml of acetic acid and 2.4 ml of water. The mixture was refluxed under nitrogen for 7 hours and filtered while hot, the solvent being distilled under reduced pressure from the filtrate. The residue was then shaken between 25 ml of water and 25 ml of chloroform. The aqueous layer was next extracted with 25 ml of chloroform three times and made alkaline by the addition of ammonia to a pH of about 8. The resultant compound was filtered, dried and purified by chromatography as described previously. The resultant product was crystallized from 90% ethanol to yield D-8-cyanomethylergoline-I as colorless needles, m.p. 273°-275° C. (decomposition), $[\alpha]_D^{20} - 49°$ C. (C=0.4 pyridine).

EXAMPLE 2—D-6-n-butyl-8-cyanomethylergoline-I

The procedure of Example 1 was repeated with the exception that n-butyl iodide was used instead of n-propyl bromide. The reaction time was 24 hours at 80°-85° C. and yielded D-6-n-butyl-8-cyanomethylergoline-I, $[\alpha]_D^{20} - 79°$ C. (C=0.4 pyridine).

EXAMPLE 3—D-6-Isopropyl-8-cyanomethylergoline-I 500 mg (3.6 mmoles) of anhydrous potassium carbonate and 3.1 grams (25 mmoles) of isopropyl bromide were added to a solution of 301 mg (1.2 mmoles) of D-8-cyanomethylergoline-I in 10 ml of dimethylformamide. The mixture was heated for 50 hours at a temperature from 95°-100° C. and the procedure of Example 1 followed. The reaction yielded D-6-isopropyl-8-cyanomethylergoline-I, m.p. 256°-258° C. (decomposition) $[\alpha]_D^{20} - 100°$ C. (C=0.4 pyridine).

EXAMPLE 4—D-6-Isobutyl-8-cyanomethylergoline-I

The procedure of Example 3 was repeated with the exception that isobutyl bromide was used as the alkylation reagent rather than isopropyl bromide. The resultant D-6-isobutyl-8-cyanomethylergoline-I evidenced a m.p. of 237°-239° C. (decomposition) (ethanol); $[\alpha]_D^{20} - 91°$ C. (C=0.4 pyridine).

EXAMPLE 5—D-6-Ethyl-8-cyanomethylergoline-I 152 mg (1.5 mmoles) of triethylamine and 232 mg (1.5 mmoles) of diethylsulfate were added to a solution of 251 mg (1 mmole) of D-8-cyanomethylergoline-I in 10 ml of anhydrous dimethylformamide and the mixture stirred at room temperature for 24 hours. The procedure of Example 1 was then followed, so yielding D-6-ethyl-8-cyanomethylergoline-I, m.p. 253°-255° C. (decomposition) (ethanol); $[\alpha]_D^{20} - 95°$ C. (C=0.4 pyridine).

EXAMPLE 6—D-6-n-Butyl-8-cyanomethylergoline-I

A mixture comprising 0.32 grams (1 mmole) D-6-n-butyl8-chloromethylergoline-I, 0.25 grams of sodium cyanide and 6.5 ml of dimethylsulfoxide were heated under nitrogen to 120° C. for 3 hours. Next, the reaction mixture was poured into 30 ml of water and the separated product filtered, heated to 65° C. with 20 ml of water for 15 minutes and, after cooling, refiltered. 0.24 grams (78% yield) of crude compound was crystallized from ethanol, yielding D-6-n-butyl-8-cyanomethylergoline-I, m.p. 187°-189° C. (decomposition); $[\alpha]_D^{20} - 79°$ C. (C=0.4 pyridine).

The D-6-n-butyl-8-chloromethylergoline-I was prepared in accordance with the following procedure:

0.11 grams of anhydrous potassium carbonate and 0.15 gram of n-butyl bromide were added to a solution of D-6-nor-9,10-dihydrolysergic acid methyl ester (0.135 g) in 7 ml of dimethylformamide and the mixture stirred at room temperature for 8 hours and maintained thereat for 24 hours. Then, the reaction mixture was poured into 400 ml of water and the precipitated product filtered, dried and crystallized from methanol, yielding D-6-nor-6-n-butyl-9,10-dihydrolysergic acid methyl ester, m.p. 169°-171° C., $[\alpha]_D^{20} - 63°$ C. (C=0.4 methanol).

0.436 g of the so-prepared methyl ester was dissolved in 120 ml of ether and the solution added dropwise under nitrogen to a stirred suspension of 0.84 g of lithium aluminum hydride in 200 ml of anhydrous ether. The resultant mixture was stirred at room temperature for 2 hours. The excess of hydride formed was destroyed by adding dropwise a mixture of 5 ml of ethanol and 1.65 ml of water, the organic portion being filtered, extracted three times with 35 ml of an 8:2 hot chloroformethanol mixture and the combined organic extracts removed under reduced pressure. The residue of 0.31 g (78%) was crystallized twice from aqueous ethanol, yielding D-6-n-butyl-8-hydroxymethylergoline-I monohydrate, m.p. 152°-154° C. It contained 5.87% of crystal water which was lost by drying at 117° C. (0.2 torr); $[\alpha]_D^{20} - 68°$ C. (C=0.5 pyridine).

0.494 g of D-6-butyl-8-hydroxymethylergoline-I and 30 ml of phosphorous oxychloride were refluxed for 1 hours. The volatile material was distilled off under reduced pressure and the residue mixed with a 5% aqueous solution of sodium hydrogen carbonate. The resultant suspension was heated to 90°-95° C. for 15 minutes, cooled and the product filtered and washed with water. A chromatographic analysis of the dried crude product on a silica gel column using chloroform with 1% of ethanol as eluant yielded 0.33 g (63%) of D-6-n-butyl-8-chloromethylergoline-I which on crystallization from a mixture of ethanol and n-hexane melted at 186°–188° C. (decomposition); $[\alpha]_D^{20} - 62°$ C. (C=0.4 pyridine).

The procedure followed in preparing the 6-n-butyl derivatives was used in preparing the following intermediates:

D-6-nor-6-n-propyl-9,10-dihydrolysergic acid methyl ester, m.p. 2.2°–2.4° C. (ethyl acetate), $[\alpha]_D^{20} - 63°$ C. (C=0.4 dichloromethane);

D-6-ethyl-8-hydroxymethylergoline-I, m.p. 252°–254° C. (ethanol-chloroform-cyclohexane), $[\alpha]_D^{20} - 91°$ C. (C=0.5 pyridine);

D-6-n-propyl-8-hydroxymethylergoline-I, m.p. 181°–182° C. (aqueous ethanol), $[\alpha]_D^{20} - 66°$ C. (C=0.5 pyridine);

D-6-ethyl-8-chloromethylergoline-I, m.p. 239°–241° C. (ethanol-hexane), $[\alpha]_D^{20} - 87°$ C. (C=0.2 pyridine); and D-6-n-propyl-8-chloromethylergoline-I, m.p. 232°–234° C. (chloroform-ethanol-cyclohexane), $[\alpha]_D^{20} - 68°$ C. (C=0.4 pyridine).

EXAMPLE 7—D-6-n-propyl-8-cyanomethylergoline-I

The procedure of Example 6 was repeated in preparing D-6-n-propyl-8-cyanomethylergoline-I, m.p. 264°–266° C. (decomposition) (ethanol), $[\alpha]_D^{20} - 83°$ C. (C=0.4 pyridine) and D-6-ethyl-8-cyanomethylergoline-I, m.p. 253°–255° C. (decomposition) (ethanol), $[\alpha]_D^{20} - 95°$ C. (C=0.4 pyridine) with the exception that D-6-n-propyl-8-cyanomethylergoline-I and D-6-ethyl-8-cyanomethylergoline-I, respectively, were employed rather than D-6-n-butyl-8-cyanomethylergoline-I.

What is claimed is:

1. D-6-alkyl-8-cyanomethylergoline-I of the formula

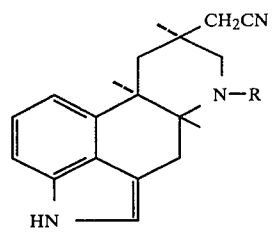

wherein R is an alkyl group of from 2–4 carbon atoms.

2. Compound of claim 1 wherein R is straight chained.
3. Compound of claim 1 wherein R is branched chained.
4. D-6-Ethyl-8-cyanomethylergoline-I.
5. D-6-n-Propyl-8-cyanomethylergoline-I.
6. D-6-Isobutyl-8-cyanomethylergoline-I.
7. Pharmaceutically acceptable salts of D-6-alkyl8-cyanomethylergoline-I of the formula

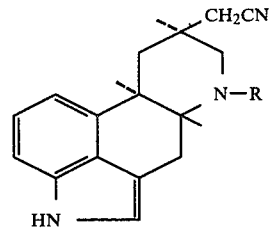

wherein R is an alkyl group of 2–4 carbon atoms, prepared by reaction of at least 1 mole-equivalent of an acid with 1 mole-equivalent of said 8-cyanomethylergoline-I in solution.

* * * * *